(12) United States Patent
Vaze

(10) Patent No.: US 9,187,709 B2
(45) Date of Patent: Nov. 17, 2015

(54) SYNTHESIS OF A NOVEL ODORANT

(76) Inventor: Kedar Ramesh Vaze, Mulund Mumbai (IN)

( * ) Notice: Subject to any disclaimer, the term of this patent is extended or adjusted under 35 U.S.C. 154(b) by 105 days.

(21) Appl. No.: 13/818,537

(22) PCT Filed: Aug. 18, 2011

(86) PCT No.: PCT/IN2011/000550
§ 371 (c)(1),
(2), (4) Date: Feb. 22, 2013

(87) PCT Pub. No.: WO2012/025934
PCT Pub. Date: Mar. 1, 2012

(65) Prior Publication Data
US 2013/0157923 A1   Jun. 20, 2013

(30) Foreign Application Priority Data
Aug. 25, 2010   (IN) .................. 2366/MUM/2010

(51) Int. Cl.
*C11B 9/00*   (2006.01)

(52) U.S. Cl.
CPC ............... *C11B 9/0034* (2013.01); *C11B 9/003* (2013.01)

(58) Field of Classification Search
CPC .............................. C11B 9/0034; C11B 9/003
USPC .......................................................... 512/22
See application file for complete search history.

(56) References Cited

U.S. PATENT DOCUMENTS

| | | | | |
|---|---|---|---|---|
| 4,962,242 A * | 10/1990 | Yamada et al. | ............... | 568/822 |
| 5,288,701 A | 2/1994 | Baudin | | |
| 5,372,995 A * | 12/1994 | Sprecker et al. | ............... | 512/20 |
| 2002/0086901 A1* | 7/2002 | Bajgrowicz et al. | .......... | 514/519 |
| 2003/0008788 A1 | 1/2003 | Sonnenberg et al. | | |
| 2010/0226871 A1* | 9/2010 | Fraser et al. | ............... | 424/70.6 |

FOREIGN PATENT DOCUMENTS

| | | |
|---|---|---|
| EP | 0258967 A2 | 3/1988 |
| JP | 05-246917 A | 9/1993 |

OTHER PUBLICATIONS

Cohen, et al. "Reductive Metallation: A General Preparative Method for Hydrocarbon Allylmetallic Compounds", Tetrahedron, vol. 42, No. 11, pp. 2803-2808, 1986.*

Kann, et al. "New Functionalized Horner-Wadsworth-Emmons Reagents: Useful Building Blocks in the Synthesis of Polyunsaturated Aldehydes", Journal of Organic Chemistry, 55, pp. 5312-5323, 1990.*

Bonnet, al. et al "Ene Diiodo Acetals: Stereoselective Synthesis of Ene Hydroxy Acetals. Handy Access to Non Conjugated Dienals", Tetrahedron, vol. 54, 1998, pp. 2743-2752.*

International Search Report for PCT/IN2011/000550, Completed by the U.S. Patent and Trademark Office on Dec. 27, 2011, 2 Pages.

Levene et al. Journal of Biological Chemistry 1935, vol. 110, p. 311-321, "The Configurational Relationship of Acids of the Phenethyl Series to Those of the Normal Series."

Bonnet B. et al, "Ene Diiodo Acetals: Stereoselective Synthesis of Ene Hydroxy Acetals. Handy Access to Non Conjugated Dienals," Tetrahedron, Elsevier Science Publishers, Amsterdam, NL, vol. 54, No. 12, Mar. 19, 1998, pp. 2743-2752, XP 004357364.

Brown, Paul et al, "Transposition of Allylic Alcohols Controlled by the Ph2PO Group: Reagents for [alpha]-Hydroxy-Diene Synthesis by the Homer-Witting Reaction," Tetrahedron Letters, vol. 26, No. 2, Jan. 1, 1985, pp. 249-252, XP055128312.

Cohen, Theodore et al., "Reductive Metallation, A General Preparative Method for Hydrocarbon Allylmetallic Compounds," Pergamon Journals, Ltd., Tetrahedron, vol. 42, No. 11, Jan. 1, 1986, pp. 2803-2808, XP055128315.

Brown, Paul et al., "The Synthesis of (Z)-Penta-2,4-dien-1-ol and Substituted (E)-Pentadienols by the Sterochemically Controlled Horner-Wittig Reaction," Journal of the Chemical Society, Perkin Transactions 1, No. 6, Jan. 1, 1991, p. 1485-1492, XP055128318.

European Search Report, Application No. 11819522.1, Date Completed, Jul. 11, 2014.

Levene, et al., "The Configurational Relationship Of MethylBenzylacetic To Methylbenzylpropionic Acid", J. Biol. Chem. 1935, pp. 299-309.

Japanese Office Action (patent application No. 2013-525422) dated Jul. 28, 2015, 3 pages, together with English Translation (3 pages).

* cited by examiner

*Primary Examiner* — Ling Choi
*Assistant Examiner* — Lanee Reuther
(74) *Attorney, Agent, or Firm* — Brooks Kushman P.C.

(57) ABSTRACT

A novel odorant of formula (I) wherein each of $R_1$, $R_2$, $R_3$, $R_4$, $R_5$, $R_6$, $R_7$, $R_8$, $R_9$ and $R_{10}$ are independently selected from H, $CH_3$, and $C_2H_5$; X is selected from —$CH_2OH$, —$CH_2OCOCH_3$ and —CHO and —CHO, n is selected from 0 and 1. The dotted line represents double bond or single bond.

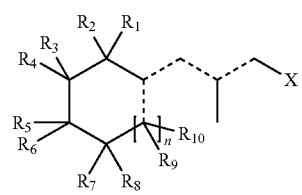

8 Claims, No Drawings

SYNTHESIS OF A NOVEL ODORANT

CROSS-REFERENCE TO RELATED APPLICATION

This application is the U.S. national phase of PCT Appln. No. PCT/IN2011/000550 filed on Aug. 18, 2011, which claims priority to IN Patent Application No. 2366/MUM/2010 filed on Aug. 25, 2010, the disclosures of which are incorporated in their entirety by reference herein.

FIELD OF THE INVENTION

The present invention relates to novel compounds possessing olfactory properties reminiscent of lily of the valley. The invention furthermore refers to a method for their production and to flavour and fragrance compositions containing these.

BACKGROUND OF THE INVENTION

It is generally known that odorants are presently utilized in the perfumery industry. Typically, these odorants are synthetic molecules based on naturally occurring fragrances. A particularly desirous and well known fragrance is "lily of the valley." In nature, several different aromas contribute to the overall fragrance profile. As such, it is difficult to achieve a single molecule that is an acceptable synthetic replacement. Unfortunately, synthesizing several molecules greatly increases the cost and complexity. While some progress has been made with regard to creating a single molecule that is an acceptable synthetic replacement for lily of the valley, these conventional odorants suffer from objectionable fragrance notes and/or short shelf-life.

It is an advantage of one or more of the embodiments of the invention that the compound exhibits a floral aroma that is similar or identical to the natural lily of the valley aroma. In addition, perfumery compositions having the novel compound described herein may exhibit a floral aroma that is similar or identical to the natural lily of the valley aroma. It is another advantage of one or more of the embodiments of the invention that the compound exhibits increased chemical stability as compared to conventional lily of the valley agents. As a result of this increased stability, the shelf life of perfumery compositions thereof are increased. In addition, this increased stability results in a corresponding increase in persistence of the aroma given off by the perfumery compositions and therefore facilitates perfumery compositions having a decreased concentration of the odorant that provides a longer lasting aroma as compared to conventional perfumery compositions.

We have now found a novel class of compounds that have a similarity to lily of the valley that is capable of overcoming the disadvantages described herein above.

SUMMARY OF THE INVENTION

The foregoing needs are met, to a great extent, by the present invention, wherein an odorant having a similarity to lily of the valley that is capable of overcoming the disadvantages described herein at least to some extent is provided.

Accordingly, in a first embodiment, there is provided compound of formula (I)

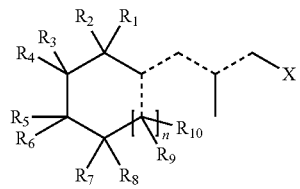

wherein each of R1, R2, R3, R4, R5, R6, R7, R8, R9 and R10 are independently selected from H, CH3, and C2H5;

X is selected from —CH2OH, —CH2OCOCH3 and —CHO;

n is selected form 0 and 1 the dotted line represents double bond or single bond.

The compounds of this invention can be used as stereoisomeric mixtures, or may be resolved in diastereomerically and/or enantiomerically pure form There has thus been outlined, rather broadly, certain embodiments of the invention in order that the detailed description thereof may be better understood herein, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

As used herein, the term "a compound of formula (I)" may refer to both a racemic mixture and the individually isolated isomers. The compounds of formula (I) may be used alone, as mixtures thereof, or in combination with a base material.

As used herein, the "base material" includes all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

The compounds according to formula (I) may be used in a broad range of fragrance applications, e.g. in any field of fine and functional perfumery, such as perfumes, air care products, household products, laundry products, body care products and cosmetics. The compounds can be employed in widely varying amounts, depending upon the specific application and on the nature and quantity of other odourant ingredients. The proportion is typically from 0.1 to 10 weight percent of the application. The compounds as described hereinabove may be employed in a consumer product base simply by directly mixing at least one compound of formula (I), or a fragrance composition with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the consumer product base. Thus, the invention additionally provides a method of manufacturing a fragrance application, comprising the incorporation of a compound of formula (I), as a fragrance ingredient, either by directly admixing the compound to the consumer product base or by admixing a fragrance composition comprising a compound of formula (I), which may then be mixed with a consumer product base, using conventional techniques and methods. Through the addition of an olfactory acceptable amount of at least one compound of the present invention as hereinabove described the odour notes of a consumer product base will be improved, enhanced, or modified.

The present disclosure relates to compound of formula (I)

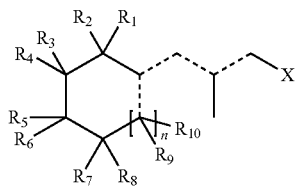

wherein each of R1, R2, R3, R4, R5, R6, R7, R8, R9 and R10 are independently selected from H, CH3, and C2H5;

X is selected from —CH2OH, —CH2OCOCH3 and —CHO;

n is selected form 0 and 1 the dotted line represents double bond or single bond.

The compounds of this invention can be used as stereoisomeric mixtures, or may be resolved in diasteremerically and/or enantiomerically pure form.

Another embodiment of the present invention relates to the compound of formula I,

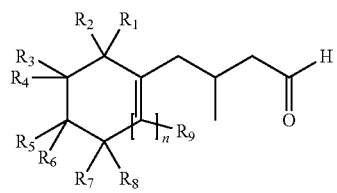

wherein each of R1, R2, R3, R4, R5, R6, R7, R8, and R9 are H.

n is selected form 0 and 1

Yet another embodiment of the present invention pertains to a compound of formula I

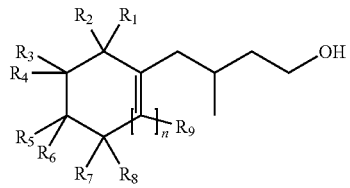

wherein each of R1, R2, R3, R4, R5, R6, R7, R8, and R9 are independently selected from the group consisting of H, CH3, and C2H5.

n is selected form 0 and 1

Yet another embodiment of the present invention pertains to an odorant including the compound of formula I.

Yet another embodiment of the present invention relates to a fragrance including the compound of formula I.

Yet another embodiment of the present invention pertains to a perfumery composition comprising an olfactory acceptable amount of the compound of formula I.

Yet another embodiment of the present invention relates to a method of synthesizing the compound of formula I.

Yet another embodiment of the present invention pertains to a perfumery composition comprising compound of formula I with at least one ingredient selected from the group consisting of solvents, carriers, stabilizers, emulsifiers, moisturizers, dispersants, diluents, thickeners, thinners, other odorants, and adjuvants.

Yet another embodiment of the present invention pertains to a method of making a perfumery composition including mixing the compound of formula I with at least one ingredient selected from the group consisting of solvents, carriers, stabilizers, emulsifiers, moisturizers, dispersants, diluents, thickeners, thinners, other odorants, and adjuvants.

Yet another embodiment of the present invention relates to a method of using a perfumery composition including applying the perfumery composition to a user.

Particular embodiments of the present invention are the compounds of formula (I) which is 4-Cyclohex-1-enyl-3-methyl-butan-1-ol
4-Cyclohex-1-enyl-3-methyl-butyraldehyde
(E)-4-Cyclohex-1-enyl-3-methyl-but-3-en-1-ol
(E)-4-Cyclohex-1-enyl-3-methyl-but-3-enal
4-Cyclohexyl-3-methyl-butan-1-ol
4-Cyclohexyl-3-methyl-butyraldehyde
(2EZ)-4-cyclohexenyl-3-methylbut-2-enal
3-Methyl-4-(3,3,5-trimethyl-cyclohexyl)-butan-1-ol
3-Methyl-4-(3,3,5-trimethyl-cyclohexyl)-butyraldehyde
(2EZ)-4-cyclohexenyl-3-methylbut-2-enyl acetate
4-cyclohexenyl-3-methylbutyl acetate
4-cyclohexyl-3-methylbutyl acetate
4-cyclopentenyl-3-methylbutyl acetate
4-cyclopentyl-3-methylbutyl acetate
4-cyclopentyl-3-methylbutan-1-ol
4-cyclopentyl-3-methylbutanal In various embodiments of the invention, the novel odorant includes a compound of formula I:

In addition, embodiments of the invention may provide a novel fragrance agent of formula I.

According to an embodiment, the present disclosure relates to a process for the preparation of a compound of formula (I), said process comprising

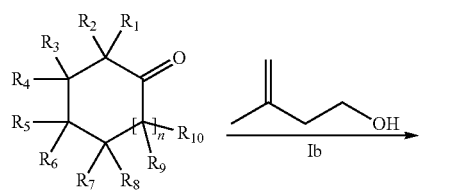

Ia

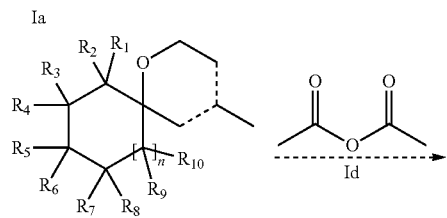

Ic

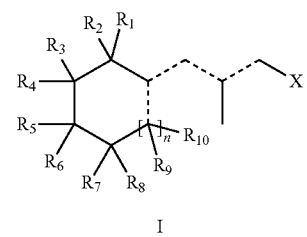

I

Compound of formula (Ia) is reacted with an alcohol of formula (Ib) to provide a compound of formula (Ic). Compound of formula (Ic) is reacted with acetic anhydride (Id) to provide compound of formula (I)

The compounds of formula (I) may be prepared following independent general synthetic routes as outlined in the Schemes 1-2

SCHEME 1:

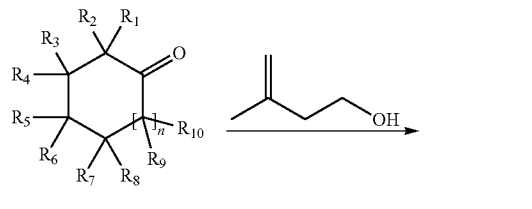

1a

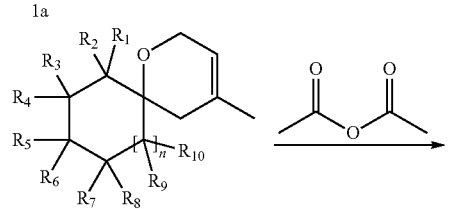

1b

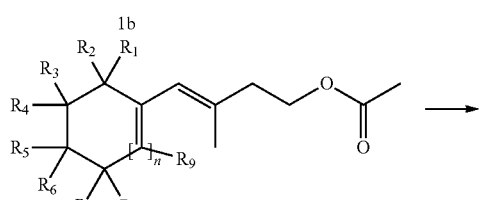

1c

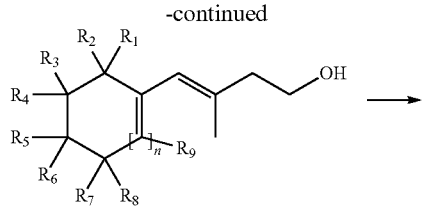

1d

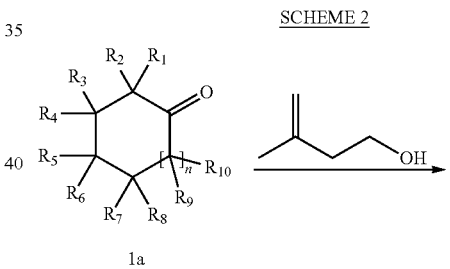

I

Compound of formula (1a) wherein all symbols are defined herein above may be reacted with 3-methyl-but-3-en-1-ol to provide compounds of formula (1b) wherein all symbols are defined herein above. Compounds of formula (1b) may be reacted with acetic anhydride to provide compound of formula (1c) which may be hydrolysed to provide compounds of formula (1d) wherein all symbols are defined herein above. Compounds of formula may be oxidized to obtain compounds of formula (I) wherein all symbols are defined herein above.

SCHEME 2

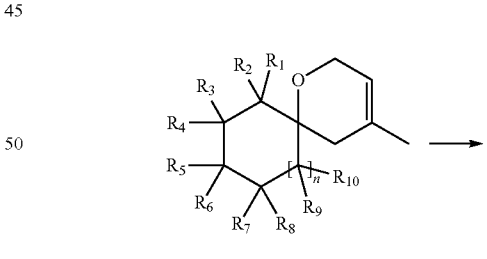

1a

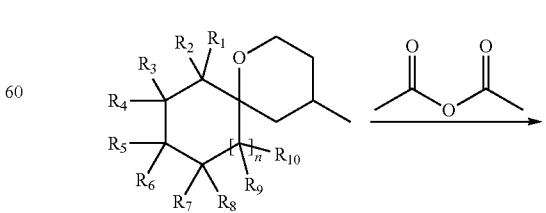

2a

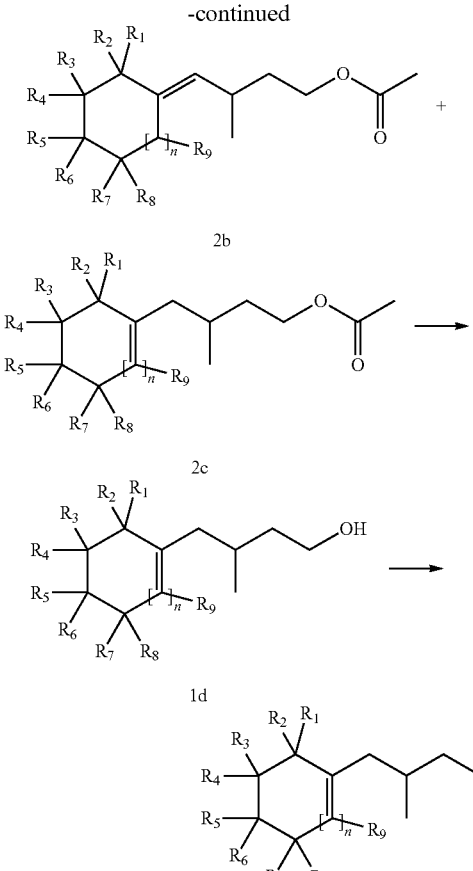

Compounds of formula (1a) wherein all symbols are defined herein above may be reacted with 3-methyl-but-3-en-1-ol to provide compounds of formula (1b) wherein all symbols are defined herein above. Compounds of formula (1b) may be hydrogenated to provide compounds of formula (2a) wherein all symbols are defined herein above. Compounds of formula (2a) may be reacted with acetic anhydride to provide a mixture of (2b) and (2c) which may be hydrolysed to provide compounds of formula (1d) wherein all symbols are defined herein above. Compounds of formula may be oxidized to obtain compounds of formula (I) wherein all symbols are defined herein above.

It will be appreciated that the compounds of formula (I) may be prepared by derivatisation of formula (I) by transformations well known to those skilled in the art, e.g functional groups such as an ester function being converted to an acid, amide, hydroxyalkyl, keto, aldehyde as well as an ester. The said conversions may be carried out using reagents and conditions well documented in the literature.

The compounds may be obtained as stereoisomeric mixtures which may be resolved in diastereomerically and/or enatiomerically pure form.

Suitable perfumery compositions generally include a perfume, a cologne, an eau du toilette, an eau du parfum, a cosmetic, a personal care product, a cleansing product, a fabric softener, an air freshener, and the like. Furthermore, it is within the purview of embodiments of the invention that the novel compound described herein may be integrated into building materials, wall and floor coverings, vehicle components, and the like.

In general, in addition to the novel odorant described herein, suitable perfumery compositions include conventional ingredients such as, for example, solvents, carriers, stabilizers, emulsifiers, moisturizers, dispersants, diluents, thickeners, thinners, other odorants, adjuvants, and the like.

EXAMPLES

The disclosure is further illustrated by the following examples which in no way should be construed as being further limiting. One skilled in the art will readily appreciate that the specific methods and results described are merely illustrative. All stereoisomers of the compounds of the instant disclosure are contemplated, either in admixture or in pure or substantially pure form. The compounds of the present disclosure can have asymmetric centers at any of the carbon atoms, consequently, compounds of formula (I) can exist in enantiomeric, or diastereomeric forms, or in mixtures thereof. The processes for preparation can utilize racemates, enantiomers, or diastereomers as starting materials. When diastereomeric or enantiomeric products are obtained as mixtures, they can be separated by conventional methods for example, chromatographic separation or fractional crystallization or through diasteriomeric salt formation. When intended, a desired enantiomer or diasteriomer can also be obtained by following appropriate enantioselective or diastereoselective reactions.

Example 1

Synthesis of 4-(cyclohex-1-en-1-yl)-3-methylbutanal via Cyclohexanone and Isoprenol

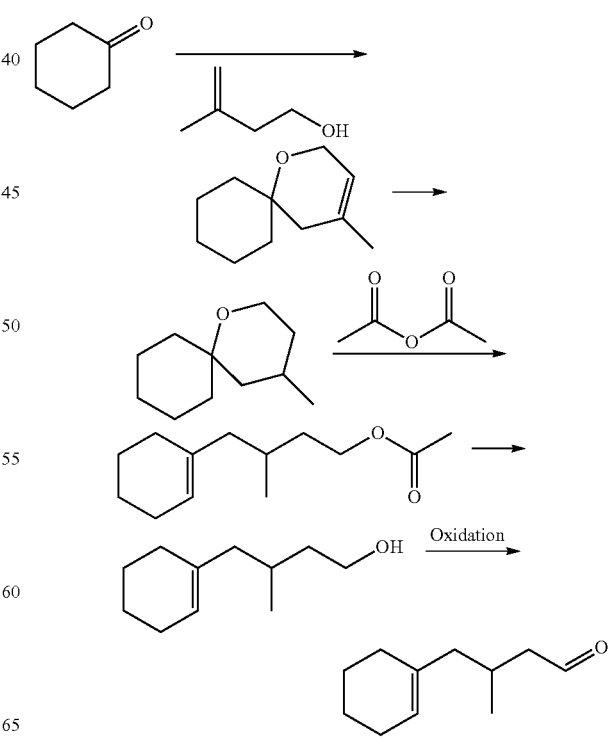

Step 1: Synthesis of 4-methyl-1-oxaspiro [5.5] undec-3-ene:

A mixture of p-TSA (20 g, 0.105 mol) and toluene (2 L) was heated to 115° C. To this mixture were added cyclohexanone (980 g, 10 mols) and isoprenol (946 g, 11 mols) and heated further for 3-6 h. Water was removed from the reaction azeotropically. The reaction mixture was then cooled to room temperature. The organic phase was washed with a 5% Na2CO3 solution, washed with water dried and concentrated and distilled further to provideto 4-methyl-1-oxaspiro [5.5] undec-3-ene (1.32 kg) having a purity of 98% (sum of the isomers) for a total yield of 80%.

Step 2: Synthesis of 4-methyl-1-oxaspiro [5.5] undecane:

A solution of 4-methyl-1-oxaspiro[5.5]undec-3-ene (1.66 kg, 10.0 mols), isopropyl alcohol (100 ml) and Raney nickel (100 g) or other suitable sponge-metal catalyst was hydrogenated at 400 psi, at 140° C. for 10-12 h until the theoretical amount of hydrogen was taken up. The mixture was cooled and filtrated. The isopropyl alcohol was evaporated and the residue obtained was distilled under reduced pressure to provide 4-methyl-1-oxaspiro [5.5] undecane (1.56 kg, yield: 93%, purity: 99% sum of the isomers).

Step 3 : Synthesis of 4-(cyclohex-1-en-1-yl)-3-methylbutyl acetate:

4-Methyl-1-oxaspiro[5.5]undecane (1.68 kg, 10.0 mols, purity: 98%) acetic anhydride (1.38 kg, 13.5 mols) and p-TSA (20 g, 0.105 mols) were mixed with continuous stirring. The temperature of the reaction mixture was raised to 125-130° C. Stirring was continued for 10-12 h. The reaction mixture was cooled to 35° C. and quenched by adding water. The aqueous phase was removed and organic phase was washed with 5% w/w aqueous sodium carbonate and twice with water. The crude product was fractionated under reduced pressure to provide the desired acetate (1.93 kg, yield: 91%; GC purity: 99% sum of the isomers).

Step 4: Synthesis of 4-(cyclohex-1-en-1-yl)-3-methyl butan-1-ol:

4-(cyclohex-1-en-1-yl)-3-methylbutyl acetate (2.1 kg, 10.0 mols, purity: 98%) sodium hydroxide (420 g, 10.5 mols) and water (8400 ml) were mixed together and heated at 90-95° C. under stirring for 10-12 h. The reaction mixture was cooled to 35° C. The aqueous phase was separated from the organic phase. The organic phase was washed once with 5% w/w aqueous NaCl and twice with water. The crude product was fractionated under reduced pressure to provide 4-(cyclohex-1-en-1-yl)-3-methyl butan-1-ol (1.5 kg, yield: 93%; GC purity: 99% sum of the isomers).

Step 5: Synthesis of 4-(cyclohex-1-en-1-yl)-3-methylbutanal:

NaBr (0.6 g, 0.006 mol) and NaHCO3 (6.4 g, 0.076 mol) were mixed together with water (60 ml), toluene (250 g) and 4-(cyclohex-1-en-1-yl)-3-methyl butan-1-ol (96 g (0.573 mol, purity: 99% sum of the isomers) at room temperature with continuous stirring. NaOCl (13% w/w aqueous 426.8 g, 0.745 mol) was added to the reaction mass over 2 h. Stirring was continued for another 1 h. The aqueous phase was removed, organic phase was washed with a solution of NaHCO3 and then with water. The organic phase thus obtained was concentrated and crude product purified by fractional distillation to provide 4-(cyclohex-1-en-1-yl)-3-methylbutanal (62.6 g, yield: 66%, GC purity: 95% sum of the isomers).

Example 2

Synthesis of (2E)-4-cyclohexenyl-3-methylbut-2-enal via Cyclohexanone and Isoprenol.

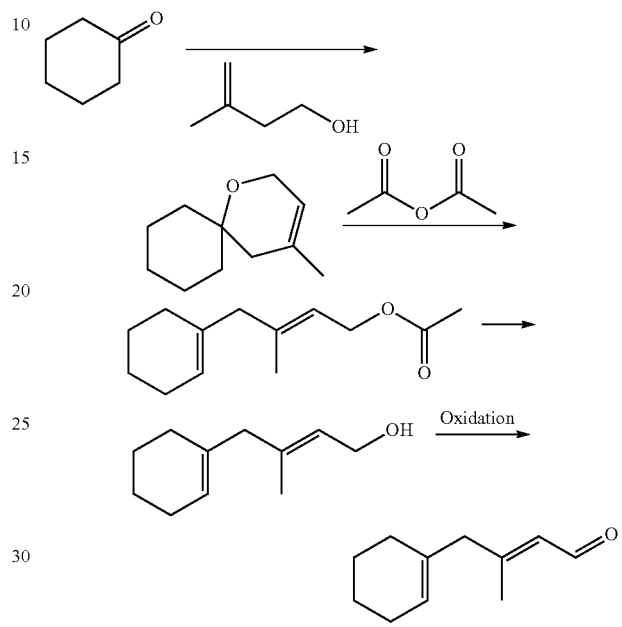

Step 1: Synthesis of 4-methyl-1-oxaspiro [5.5] undec-3-ene:

A mixture of p-TSA (20 g, 0.105 mol) and toluene (2 L) was heated to 115° C. To this mixture were added cyclohexanone (980 g, 10 mols) and isoprenol (946 g, 11 mols) and heated further for 3-6 h. Water was removed from the reaction azeotropically. The reaction mixture was then cooled to room temperature. The organic phase was washed with a 5% Na2CO3 solution, washed with water dried and concentrated and distilled further to provide 4-methyl-1-oxaspiro [5.5] undec-3-ene (1.32 kg) having a purity of 98% (sum of the isomers) for a total yield of 80%.

Step 2: Synthesis of (2E)-4-cyclohexenyl-3-methylbut-2-enyl acetate:

4-Methyl-1-oxaspiro[5.5]undecane (1.66 kg, 10.0 mols, purity: 98%) acetic anhydride (13.33 kg, 130.0 mols) and p-TSA (332 g, 1.75 mols) were mixed with continuous stirring. The reaction mixture stirred at room temperature (25° C). Stirring was continued for 4-5 h. The reaction mixture was quenched by adding water. The aqueous phase was removed and organic phase was washed with 5% w/w aqueous sodium carbonate and twice with water. The crude product was fractionated under reduced pressure to provide the desired acetate (1.12 kg, yield: 54%; GC purity: 95% sum of the isomers).

Step 3: Synthesis of (2E)-4-cyclohexenyl-3-methylbut-2-en-1-ol:

(2E)-4-cyclohexenyl-3-methylbut-2-enyl acetate (2.08 kg, 10.0 mols, purity: 98%) sodium hydroxide (420 g, 10.5 mols) and water (8400 ml) were mixed together and heated at 90-95° C. under stirring for 10-12 h. The reaction mixture was cooled to 35° C. The aqueous phase was separated from the organic phase. The organic phase was washed once with 5% w/w aqueous NaCl and twice with water. The crude product was fractionated under reduced pressure to provide (2E)-4-cyclohexenyl-3-methylbut-2-en-1-ol (1.5 kg, yield: 93%; GC purity: 99% sum of the isomers). Reduced pressure (1 mmHg) to give 1.54 kg of (2E)-4-(cyclohex-1-en-1-yl)-3-methylbut-3-en-1-ol and (2E) isomer (yield: 93%; GC purity: 99% sum of the isomers).

Step 4: Synthesis of (2E)-4-cyclohexenyl-3-methylbut-2-enal:

NaBr (0.6 g, 0.006 mol) and NaHCO3 (6.4 g, 0.076 mol) were mixed together with water (60 ml), toluene (250 g) and (2E)-4-cyclohexenyl-3-methylbut-2-en-1-ol (96 g (0.573 mol, purity: 99% sum of the isomers) at room temperature with continuous stirring. NaOCl (13% w/w aqueous 426.8 g, 0.745 mol) was added to the reaction mass over 2 h. Stirring was continued for another 1 h. The aqueous phase was removed, organic phase was washed with a solution of NaHCO3 and then with water. The organic phase thus obtained was concentrated and crude product purified by fractional distillation to provide (2E)-4-cyclohexenyl-3-methylbut-2-enal (62.6 g, yield: 66%, GC purity: 95% sum of the isomers).

Example 3

Synthesis of 4-(cyclohex-1-en-1-yl)-3-methylbutanal via Cyclohexanone and Isoprenol

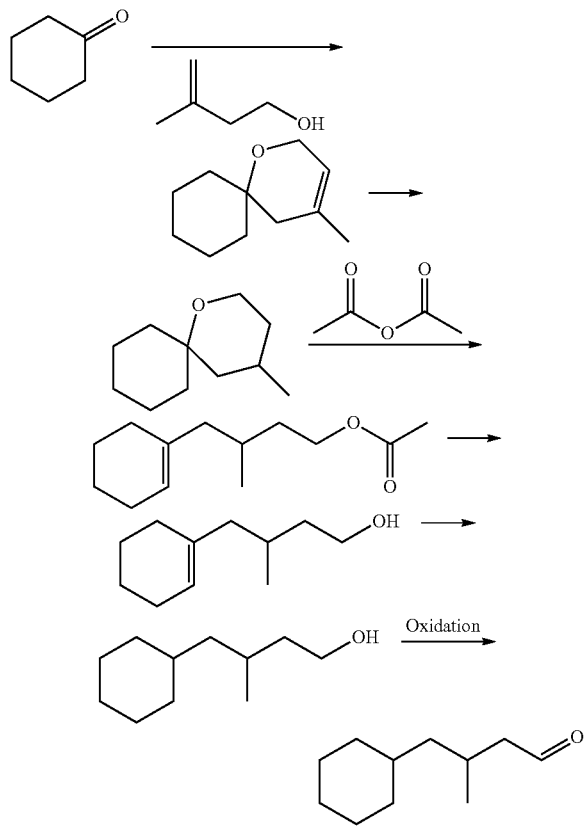

Step 1: Synthesis of 4-methyl-1-oxaspiro [5.5] undec-3-ene:
A mixture of p-TSA (20 g, 0.105 mol) and toluene (2 L) was heated to 115° C. To this mixture were added cyclohex-anone (980 g, 10 mols) and isoprenol (946 g, 11 mols) and heated further for 3-6 h. Water was removed from the reaction azeotropically. The reaction mixture was then cooled to room temperature. The organic phase was washed with a 5% Na2CO3 solution, washed with water dried and concentrated and distilled further to provideto 4-methyl-1-oxaspiro [5.5] undec-3-ene (1.32 kg) having a purity of 98% (sum of the isomers) for a total yield of 80%.

Step 2: Synthesis of 4-methyl-1-oxaspiro [5.5]undecane:
A solution of 4-methyl-1-oxaspiro[5.5]undec-3-ene (1.66 kg, 10.0 mols), isopropyl alcohol (100 ml) and Raney nickel (100 g) or other suitable sponge-metal catalyst was hydrogenated at 400 psi, at 140° C. for 10-12 h until the theoretical amount of hydrogen was taken up. The mixture was cooled and filtrated. The isopropyl alcohol was evaporated and the residue obtained was distilled under reduced pressure to provide 4-methyl-1-oxaspiro [5.5] undecane (1.56 kg, yield: 93%, purity: 99% sum of the isomers).

Step 3: Synthesis of 4-(cyclohex-1-en-1-yl)-3-methylbutyl acetate:
4-Methyl-1-oxaspiro[5.5]undecane (1.68 kg, 10.0 mols, purity: 98%) acetic anhydride (1.38 kg, 13.5 mols) and p-TSA (20 g, 0.105 mols) were mixed with continuous stirring. The temperature of the reaction mixture was raised to 125-130° C. Stirring was continued for 10-12 h. The reaction mixture was cooled to 35° C. and quenched by adding water. The aqueous phase was removed and organic phase was washed with 5% w/w aqueous sodium carbonate and twice with water. The crude product was fractionated under reduced pressure to provide the desired acetate (1.93 kg, yield: 91%; GC purity: 99% sum of the isomers).

Step 4: Synthesis of 4-(cyclohex-1-yl)-3-methyl butan-1-ol:
4-(cyclohex-1-en-1-yl)-3-methylbutyl acetate (2.1 kg, 10.0 mols, purity: 98%) sodium hydroxide (420 g, 10.5 mols) and water (8400 ml) were mixed together and heated at 90-95° C. under stirring for 10-12 h. The reaction mixture was cooled to 35° C. The aqueous phase was separated from the organic phase. The organic phase was washed once with 5% w/w aqueous NaCl and twice with water. The crude product was fractionated under reduced pressure to provide 4-(cyclohex-1-en-1-yl)-3-methyl butan-1-ol (1.5 kg, yield: 93%; GC purity: 99% sum of the isomers).

Step 5: Synthesis of 4-(cyclohex-1-en-1-yl)-3-methylbutan-1-ol:
A solution of 4-(cyclohex-1-en-1-yl)-3-methylbutan-1-ol (1.68 kg, 10.0 mols), isopropyl alcohol (100 ml) and Raney nickel (100 g) or other suitable sponge-metal catalyst was hydrogenated at 400 psi, at 140° C. for 10-12 h until the theoretical amount of hydrogen was taken up. The mixture was cooled and filtrated. The isopropyl alcohol was evaporated and the residue obtained was distilled under reduced pressure to provide 4-(Cyclohex-1-yl)-3-methylbutan-1-ol (1.58 kg, yield: 93%, purity: 99% sum of the isomers).

Step 6: Synthesis of 4-(Cyclohex-1-yl)-3-methylbutanal:
KBr (0.6 g, 0.005 mol) and NaHCO3 (6.4 g, 0.076 mol) and 0.8 g (0.00566 mols) 2,2,6,6-Tetramethylpiperidine-1-oxyl (TEMPO) were mixed together with water (60 ml), toluene (250 g) and 4-(cyclohex-1-yl)-3-methyl butan-1-ol (96 g 0.564 mol, purity: 99% sum of the isomers) the reaction temperature maintain 0° C. with continuous stirring. NaOCl (13% w/w aqueous 426.8 g, 0.745 mol) was added to the reaction mass over 2 h. Stirring was continued for another 12 h. The aqueous phase was removed, organic phase was washed with a solution of NaHCO3 and then with water. The organic phase thus obtained was concentrated and crude product purified by fractional distillation to provide 4-(Cyclohex-1-yl)-3-methylbutanal (42.63 g, yield: 45%, GC purity: 95%).

Example 4

Synthesis of 3-Methyl-4(3,3,5-trimethylcyclohexyl)butanal via Cyclohexanone and Isoprenol

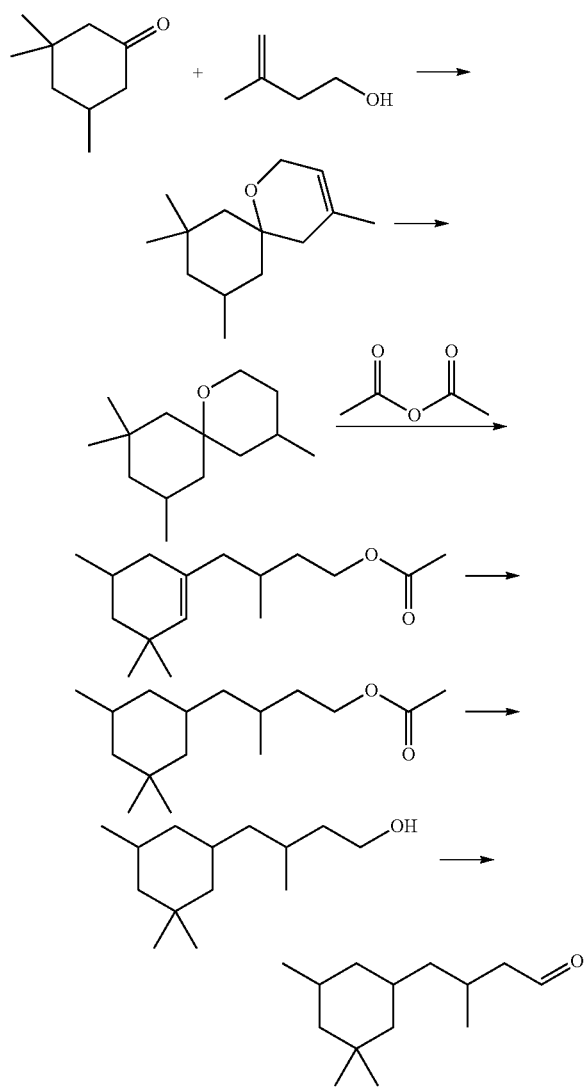

Step 1: Synthesis of 4,8,8,10-Tetramethyl-1-oxaspiro [5.5] undec-3-ene:

A mixture of p-TSA (20 g, 0.105 mol) and toluene (2 L) was heated to 115° C. To this mixture were added 3,3,5-trimethyl cyclohexanone (1.4 kg, 10 mols) and isoprenol (946 g, 11 mols) and heated further for 3-6 h. Water was removed from the reaction azeotropically. The reaction mixture was then cooled to room temperature. The organic phase was washed with a 5% Na2CO3 solution, washed with water dried and concentrated and distilled further to provide to 4,8,8,10-tetramethyl-1-oxaspiro [5.5] undec-3-ene (1.45 kg) having a purity of 94% (sum of the isomers) for a total yield of 55%.

Step 2: Synthesis of 4,8,8,10-Tetramethyl-1-oxaspiro [5.5] undecane:

A solution of 4,8,8,10-tetramethyl-2-oxaspiro [5.5] undec-3-ene (2.08 kg, 10.0 mols), isopropyl alcohol (1000 ml) and Raney nickel (100 g) or other suitable sponge-metal catalyst was hydrogenated at 400 psi, at 140° C. for 10-12 h until the theoretical amount of hydrogen was taken up. The mixture was cooled and filtrated. The isopropyl alcohol was evaporated and the residue obtained was distilled under reduced pressure to provide 4,8,8,10-Tetramethyl-1-oxaspiro[5.5] undecane (1.89 kg, yield: 90%, purity: 97% sum of the isomers).

Step 3: Synthesis of 3-Methyl-4(3,3,5-trimethylcyclohex-1-en-1-yl) butyl acetate:

4,8,8,10-Tetramethyl-2-oxaspiro [5.5] undecane (2.1 kg, 10.0 mols, purity: 98%) acetic anhydride (13.33 kg, 130.0 mols) and p-TSA (332 g, 1.75 mols) were mixed with continuous stirring. The temperature of the reaction mixture was raised to 125-130° C. Stirring was continued for 10-12 h. The reaction mixture was cooled to 35° C. and quenched by adding water. The aqueous phase was removed and organic phase was washed with 5% w/w aqueous sodium carbonate and twice with water. The crude product was fractionated under reduced pressure to provide the desired acetate (1.76 kg, yield: 70%; GC purity: 95% sum of the isomers).

Step 4: Synthesis of 3-Methyl-4-(3,3,5-trimethylcyclohex-1-yl) butyl acetate:

A solution of 3-Methyl-4-(3,3,5-trimethylcyclohex-1-en-1-yl) butyl acetate (2.52 kg, 10.0 mols), isopropyl alcohol (1000 ml) and Raney nickel (100 g) or other suitable sponge-metal catalyst was hydrogenated at 400 psi, at 140° C. for 10-12 h until the theoretical amount of hydrogen was taken up. The mixture was cooled and filtrated. The isopropyl alcohol was evaporated and the residue obtained was distilled under reduced pressure to provide 3-Methyl-4(3,3,5-trimethylcyclohexyl)butyl acetate (2.36 kg, yield: 93%, purity: 97% sum of the isomers).

Step 5: Synthesis of 3-Methyl-4(3,3,5-trimethylcyclohex-1-yl) butan-1-ol:

3-Methyl-4(3,3,5-trimethylcyclohex-1-yl)butyl acetate (2.54 kg, 10.0 mols, purity: 97%) sodium hydroxide (420 g, 10.5 mols) and water (8400 ml) were mixed together and heated at 90-95° C. under stirring for 10-12 h. The reaction mixture was cooled to 35° C. The aqueous phase was separated from the organic phase. The organic phase was washed once with 5% w/w aqueous NaCl and twice with water. The crude product was fractionated under reduced pressure to provide 3-Methyl-4(3,3,5-trimethylcyclohex-1-yl) butan-1-ol (1.95 kg, yield: 92%; GC purity: 98% sum of the isomers).

Step 6: Synthesis of 3-Methyl-4(3,3,5-trimethylcyclohexyl) butanal:

KBr (0.6 g, 0.005 mol) and NaHCO3 (6.4 g, 0.076 mol) and 0.8 g (0.00566 mols) 2,2,6,6-Tetramethylpiperidine-1-oxyl (TEMPO) were mixed together with water (60 ml), toluene (250 g) and 3-Methyl-4(3,3,5-trimethylcyclohex-1-yl) butan-1-ol (96 g 0.45 mol, purity: 98% sum of the isomers) the reaction temperature maintain 0° C. with continuous stirring. NaOCl (13% w/w aqueous 426.8 g, 0.745 mol) was added to the reaction mass over 2 h. Stirring was continued for another 12 h. The aqueous phase was removed, organic phase was washed with a solution of NaHCO3 and then with water. The organic phase thus obtained was concentrated and crude product purified by fractional distillation to provide 3-Methyl-4(3,3,5-trimethylcyclohexyl) butanal (42.63 g, yield: 45%, GC purity: 96% sum of isomers).

Example 5

Synthesis of 4-cyclopentyl-3-methylbutanal via Cyclopentanone and Isoprenol

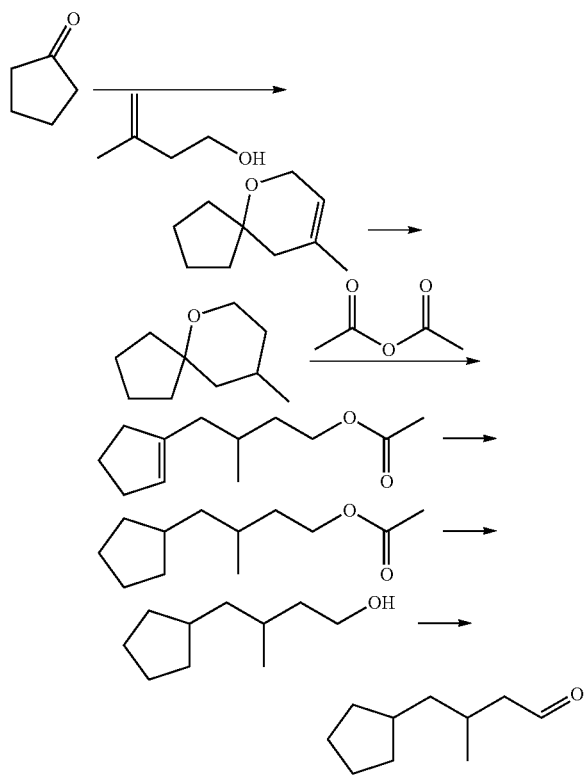

Step 1: Synthesis of 9-methyl-6-oxaspiro[4.5]dec-8-ene:

A mixture of p-TSA (20 g, 0.105 mol) and toluene (2 L) was heated to 115° C. To this mixture were added cyclopentanone (840 g, 10 mols) and isoprenol (946 g, 11 mols) and heated further for 3-6 h. Water was removed from the reaction azeotropically. The reaction mixture was then cooled to room temperature. The organic phase was washed with a 5% Na2CO3 solution, washed with water dried and concentrated and distilled further to provideto 9-methyl-6-oxaspiro[4.5]dec-8-ene (0.851 kg) having a purity of 95% (sum of the isomers) for a total yield of 56%.

Step 2: Synthesis of 9-methyl-6-oxaspiro[4.5]decane:

A solution of 9-methyl-6-oxaspiro[4.5]dec-8-ene (1.52 kg, 10.0 mols), isopropyl alcohol (1000 ml) and Raney nickel (100 g), Pd/C (100 g) or other suitable sponge-metal catalyst was hydrogenated at 450 psi, at 140° C. for 10-12 h until the theoretical amount of hydrogen was taken up. The mixture was cooled and filtrated. The isopropyl alcohol was evaporated and the residue obtained was distilled under reduced pressure to provide 9-methyl-6-oxaspiro[4.5]decane (1.4 kg, yield: 95%, purity: 98%).

Step 3: Synthesis of 4-cyclopentenyl-3-methylbutyl acetate:

9-methyl-6-oxaspiro[4.5]decane (1.54 kg, 10.0 mols, purity: 98%) acetic anhydride (1.38 kg, 13.5 mols) and p-TSA (20 g, 0.105 mols) were mixed with continuous stirring. The temperature of the reaction mixture was raised to 125-130° C. or room temp. Stirring was continued for 10-12 h. The reaction mixture was cooled to 35° C. and quenched by adding water. The aqueous phase was removed and organic phase was washed with 5% w/w aqueous sodium carbonate and twice with water. The crude product was fractionated under reduced pressure to provide the desired acetate (1.56 kg, yield: 80%; GC purity: 99% sum of the isomers).

Step 4: Synthesis of 4-cyclopentyl-3-methylbutyl acetate:

A solution of 4-cyclopentenyl-3-methylbutyl acetate (1.96 kg, 10.0 mols), isopropyl alcohol (1000 ml) and Raney nickel (100 g), Pd/C 100 g) or other suitable sponge-metal catalyst was hydrogenated at 400 psi, at 140° C. for 10-12 h until the theoretical amount of hydrogen was taken up. The mixture was cooled and filtrated. The isopropyl alcohol was evaporated and the residue obtained was distilled under reduced pressure to provide 4-cyclopentyl-3-methylbutyl acetate (1.84 kg, yield: 93%, purity: 98%.

Step 5: Synthesis of 4-cyclopentyl-3-methylbutan-1-ol:

4-cyclopentyl-3-methylbutyl acetate (1.98 kg, 10.0 mols, purity: 98%) sodium hydroxide (420 g, 10.5 mols) and water (8400 ml) were mixed together and heated at 90-95° C. under stirring for 10-12 h. The reaction mixture was cooled to 35° C. The aqueous phase was separated from the organic phase. The organic phase was washed once with 5% w/w aqueous NaCl and twice with water. The crude product was fractionated under reduced pressure to provide 4-cyclopentyl-3-methylbutan-1-ol (1.43 kg, yield: 92%; GC purity: 99%).

Step 6: Synthesis of 4-cyclopentyl-3-methylbutanal:

KBr (0.6 g, 0.005 mol) and NaHCO3 (6.4 g, 0.076 mol) and 0.8 g (0.00566 mols) 2,2,6,6-Tetramethylpiperidine-1-oxyl (TEMPO) were mixed together with water (60 ml), toluene (250 g) and 4-cyclopentyl-3-methylbutan-1-ol (70.2 g 0.45 mol, purity:98%) the reaction temperature maintain 0° C. with continuous stirring. NaOCl (12% w/w aqueous 426.8 g, 0.745 mol) was added to the reaction mass over 2 h. Stirring was continued for another 12 h. The aqueous phase was removed, organic phase was washed with a solution of NaHCO3 and then with water. The organic phase thus obtained was concentrated and crude product purified by fractional distillation to provide 4-cyclopentyl-3-methylbutanal (41.58 g, yield: 60%, GC purity: 97%)

Preparation of Perfumery Compositions

A perfumery composition, having a fresh floral character, was prepared by admixing the following ingredients:

| Ingredients | Parts by weights |
| --- | --- |
| Benzyl acetate | 100 |
| 50%* benzoin Sumatra essential oil | 80 |
| Bergamot essential oil | 150 |
| Citral | 50 |
| Coumarin | 50 |
| Geraniol | 350 |
| 1,3-benzodioxole-5-cardaldehyde | 50 |
| Lemongrass | 100 |
| Compound of formula (I) | 20 |

*In dipropyleneglycol

The addition of 20 parts by weight of product comprising of our claimed general formula to the above described perfuming composition imparted to the latter a fresh floral aspect increasing both the volume and the perceived diffusion of the fragrance.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A perfumery composition comprising a compound of formula (I)

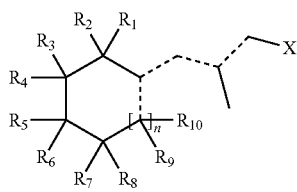

(I)

wherein each of $R_1$, $R_2$, $R_3$, $R_4$, $R_5$, $R_6$, $R_7$, $R_8$, $R_9$ and $R_{10}$ are independently selected from the group consisting of H, $CH_3$, and $C_2H_5$, X is —CHO, n is selected from the group consisting of 0 and 1, and the dotted line represents a double bond or a single bond.

2. A perfumery composition of claim 1 further comprising at least one ingredient selected from the group consisting of solvents, carriers, stabilizers, emulsifiers, moisturizers, dispersants, diluents, thickeners, thinners, other odorants, and adjuvants.

3. The perfumery composition of claim 2 wherein the compound is present in about 0.1 to about 10 weight percent of the perfumery composition.

4. The perfumery composition of claim 1 wherein the compound is present in about 0.1 to about 10 weight percent of the perfumery composition.

5. A process for preparation of the perfumery composition according to claim 1, wherein the process comprises following steps:

reacting a compound of formula (Ia)

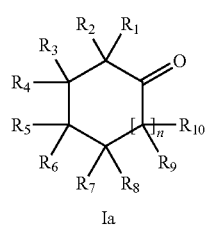

(Ia)

with an alcohol of formula (Ib)

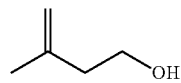

(Ib)

to receive a compound of formula (Ic)

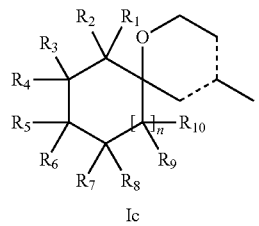

(Ic)

and reacting the compound of formula (Ic) with an acetic anhydride to receive the compound of formula (I).

6. An odorant comprising a compound of formula (I)

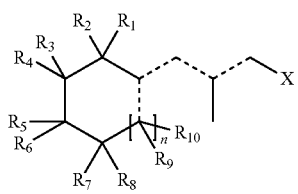

(I)

wherein each of $R_1$, $R_2$, $R_3$, $R_4$, $R_5$, $R_6$, $R_7$, $R_8$, $R_9$ and $R_{10}$ are independently selected from the group consisting of H, $CH_3$, and $C_2H_5$, X is —CHO, n is selected from the group consisting of 0 and 1, and the dotted line represents a double bond or a single bond.

7. A fragrance comprising a compound of formula (I)

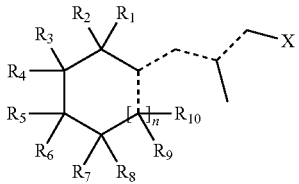

(I)

wherein each of $R_1$, $R_2$, $R_3$, $R_4$, $R_5$, $R_6$, $R_7$, $R_8$, $R_9$ and $R_{10}$ are independently selected from the group consisting of H, $CH_3$, and $C_2H_5$, X is —CHO, n is selected from the group consisting of 0 and 1, and the dotted line represents a double bond or a single bond.

8. The fragrance of claim 7 wherein the compound is present in about 0.1 to about 10 weight percent of the fragrance.

* * * * *